(12) United States Patent
Becker et al.

(10) Patent No.: US 7,570,983 B2
(45) Date of Patent: Aug. 4, 2009

(54) METHOD AND DATA PROCESSING DEVICE TO SUPPORT DIAGNOSIS AND/OR THERAPY OF A PATHOLOGICAL CHANGE OF A BLOOD VESSEL

(75) Inventors: Christoph Becker, Starnberg (DE); Roman Fischbach, Muenster (DE); Thomas Flohr, Uehlfeld (DE); Andreas Kopp, Tuebingen (DE); Bernd Ohnesorge, Erlangen (DE); Stefan Schaller, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 1229 days.

(21) Appl. No.: 10/693,586

(22) Filed: Oct. 24, 2003

(65) Prior Publication Data
US 2004/0133094 A1 Jul. 8, 2004

(30) Foreign Application Priority Data
Oct. 24, 2002 (DE) .............................. 102 49 643

(51) Int. Cl.
*A61B 5/00* (2006.01)
(52) U.S. Cl. ....................... 600/407; 600/410; 600/425; 600/441; 600/476; 600/478; 382/128
(58) Field of Classification Search ................. 600/407, 600/410, 425, 441, 476, 478; 382/128
See application file for complete search history.

(56) References Cited
U.S. PATENT DOCUMENTS
4,141,347 A * 2/1979 Green et al. ................. 600/441
(Continued)

FOREIGN PATENT DOCUMENTS
WO  WO 01/93745  12/2001

OTHER PUBLICATIONS

"Volumetric Coronary Plaque Composition using Intravascular Ultrasound: Three-Dimensional Segmentation and Spectral Analysis," Klingensmith et al, Computer in Cardiology, vol. 29 (2002), pp. 113-116.

(Continued)

*Primary Examiner*—Long V Le
*Assistant Examiner*—Baisakhi Roy
(74) *Attorney, Agent, or Firm*—Schiff Hardin LLP (57) ABSTRACT

In a method to support the diagnosis and/or therapy of a pathological change of a blood vessel of a patient, in particular in the context of coronary heart disease at a first point in time of a pixel-based or voxel-based first image is acquired with the blood vessel of interest by an imaging method, a determination is made from the first image of a quantity of existing non-calcified plaque and a quantity of existing calcium-rich plaque, a determination of a first indicator value is made from the quantities of the different plaque types that represents a measurement of the quantity and the composition of plaque present in the blood vessel at the first point in time, a comparison of the first indicator value is made with at least one limit value stored in a storage of a data processing device, and dependent on the comparison, a presentation is made on an output unit associated with the electronic data processing device of either a proposal for a measure to be undertaken on the patient, or a proposal for no measure.

33 Claims, 3 Drawing Sheets

U.S. PATENT DOCUMENTS

| | | | |
|---|---|---|---|
| 4,945,478 A | | 7/1990 | Merickel et al. |
| 5,935,075 A | * | 8/1999 | Casscells et al. ............ 600/474 |
| 6,120,515 A | * | 9/2000 | Rogers et al. ............... 606/159 |
| 6,922,462 B2 | * | 7/2005 | Acharya et al. .......... 378/98.11 |
| 2003/0176780 A1 | * | 9/2003 | Arnold et al. ............... 600/407 |
| 2003/0191398 A1 | * | 10/2003 | Motz et al. .................. 600/478 |
| 2004/0073120 A1 | * | 4/2004 | Motz et al. .................. 600/478 |
| 2004/0133094 A1 | * | 7/2004 | Becker et al. ............... 600/407 |
| 2004/0133100 A1 | * | 7/2004 | Naghavi et al. ............. 600/425 |
| 2005/0096528 A1 | * | 5/2005 | Fritz et al. .................. 600/407 |
| 2006/0100502 A1 | * | 5/2006 | Chen et al. .................. 600/419 |
| 2007/0167836 A1 | * | 7/2007 | Scepanovic et al. .......... 600/476 |
| 2008/0154117 A1 | * | 6/2008 | Nielles-Vallespin ......... 600/410 |
| 2008/0294037 A1 | * | 11/2008 | Richter ....................... 600/424 |

OTHER PUBLICATIONS

"Quantification of Coronary Artery Calcium Using Ultrafast Computed Tomography," Agataston et al, J. Amer. Coll, of Cardiology, vol. 16 (1990), pp. 827-832.

"Non-Invasive In Vivo Human Coronary Artery Lumen and Walk-Imaging Using Black-Blood Magnetic Resonance Imaging," Fayad et al, Circulation, vol. 102 (2000) pp. 506-510.

"Cardiac Imaging by Means of Electrocardiographically Gated Multisection Spiral CT: Initial Experience," Ohnesorge et al, Radiology, vol. 217 (2002), pp. 564-571.

"Current Development of Cardiac Imaging With Multidetector-Row CT," Becker et al, Europ. J. of Radiology, vol. 36 (2000) pp. 97-103.

"Non-Invasive Detection and E valuation of Atherosclerotic Coronary Plaques With Multi-slice Computed Tomography," Schröder et al, J. Amer. Coll. Of Cardiology, vol. 37 (2001) pp. 1430-1435.

* cited by examiner

METHOD AND DATA PROCESSING DEVICE TO SUPPORT DIAGNOSIS AND/OR THERAPY OF A PATHOLOGICAL CHANGE OF A BLOOD VESSEL

BACKGROUND OF THE INVENTION

1. Field of the Invention

The present invention concerns a method to support the diagnosis and/or therapy of a pathological change of a blood vessel of a patient, in particular in the context of coronary heart disease, as well as a data processing device for such a purpose.

2. Description of the Prior Art

Blood vessels, in particular coronary blood vessels, for example coronary arteries, are affected by coronary heart disease, one of the main causes of death in the industrial nations. For example, over one million people in Europe and the USA died in the year 2000 as a result of a heart attack. The causes of coronary heart disease are atherosclerotic plaques in the coronary vessels that can lead to vasoconstrictions (narrowing) or vascular occlusion.

It is known that atherosclerotic plaques occur in various types with compositions different from one another. In general, they are differentiated by:

a) lipid-rich or non-calcified plaques, also designated as soft or "vulnerable" plaques: these types of plaques are associated with a particularly high risk for a coronary event (attack, sudden cardiac death), because with high probability, their rupture leads to an acute vascular occlusion, for example to a thrombotic occlusion or to an acute myocardial attack. The goal of the use of specific medicines, known as lipid suppressors, is the reduction of the risk of an acute coronary event that can lead to sudden cardiac death. The goal of the pharmacological therapy is the stabilization of potentially unstable plaques as well as the regression of advanced lesions. The effect of the lipid suppressors is currently not known in detail, such that the requirement exists to observe their effect in each individual case.

b) fibrous plaque: atherosclerotic plaques can change their composition, i.e. their type, over the course of time. A fibrous plaque represents a state between "lipid-rich" and "calcified" (see following) plaque.

c) calcified plaque: a plaque that has calcified—and likewise also a fibrous plaque—is in general stable and seldom causes acute vascular occlusion.

A need thus exists to detect an existing plaque in a patient in order to be able to evaluate the risk associated therewith as to the occurrence of coronary events. One method for detection of calcified plaques in the coronary arteries is described in the professional article by Agatston A. S., Janowitz W. R., Hildner F. J., Zusmer N. R., Viamonte M., Detrano R., "Quantification of coronary artery calcium using ultrafast computed tomography", Journal of the American College of Cardiology (1990), volume 15, pages 827-832. Electron beam computed tomography (EBCT) is used as an imaging method. The detection of non-calcified plaques with EBCT can currently not be achieved due to the severely limited contrast resolution.

The detection of non-calcified coronary plaques is possible, for example, using the technique of intravascular ultrasound (IVUS). A running differentiation of atherosclerotic plaques (but only indirectly by a determination of wall thickness) also can ensue by means of magnetic resonance tomography. Such a method is specified in the professional article by Fayad A. A., Fuster V., Fallon J. T., "Non-invasive in vivo human coronary artery lumen and wall imaging using black-blood magnetic resonance imaging", Circulation (2000) volume 102, pages 506-510.

The newest generation of the multi-slice (multi-layer) computed tomography devices (MDCT) likewise allow the non-invasive depiction of the coronary arteries. With regard to this, electrocardiogram-synchronized (ECG-synchronized) acquisition techniques are described in the professional article by Ohnesorge B., Flohr T., Becker C. R., Kopp A. F., Knez A., Baum U., Klingenbeck-Regn K., Reiser M. F., "Cardiac Imaging by Means of Electrocardiographically Gated Multisection Spiral CT: Initial Experience", Radiology (2002), volume 217, pages 564-571. As is presented in the professional article by Becker C. R., Ohnesorge B., Schöpf U. J., Reiser M. (2002c), "Current Development of Cardiac Imaging with Multidetector-Row CT", European Journal of Radiology (2000), volume 36, pages 97-103, the depiction of calcified and non-calcified plaques with multi-slice computer tomography is possible on the basis of approximate isotropic section cross-section data sets. In the professional article by Schröder S., Kopp A. F., Baumbach A., Küttner A., Georg C., Ohnesorge B., Herdeg C., Claussen C. D., Karsch K. R., "Non-invasive Detection and Evaluation of Atherosclerotic Plaque with Multi-Slice Computed Tomography", Journal of the American College of Cardiology (2001), volume 37, pages 1430-1435 it is disclosed that lipid-rich, fibrous and calcified plaques can be differentiated via measurement of the CT density values.

SUMMARY OF THE INVENTION

An object of the present invention is to provide a method and a data processing device with which the diagnosis and/or therapy of a pathological change of a blood vessel, in particular in the context of coronary heart disease, can be supported.

This object is achieved according to the invention in a method wherein a) at a first point in time a pixel-based or voxel-based first image is acquired with the blood vessel of interest by means of an imaging method, b) a measurement of the existing amount of non-calcified plaque and a measurement of the existing quantity of calcium-rich plaque are determined from the first image, c) a first indicator value is determined from the quantities of the different plaque types that represents a measurement of the quantity and the composition of plaque present in the blood vessel at the first point in time, d) the first indicator value is compared with at least one limit value stored in a memory of a data processing device, and e) on an output unit associated with the electronic data processing device, a presentation is made that contains dependent on the comparison either a proposal for a measure to be undertaken on the patient, or a proposal for no measure.

The invention is based on the recognition that an indicator number can be formed that measures or estimates both calcified and lipid plaque. Furthermore, it is based on the recognition that this indicator number is suitable as a risk measurement category and can be used in an automated process as a decision criterion in order to give the doctor a decision aid at hand. The method thus also represents a method for generation of estimation data for risk evaluation, in particular also in the framework of a prophylactic. In particular, it can be fashioned as a method for operation of an imaging medical device.

Magnetic resonance technology, computed tomography or x-ray angiography, for example with C-arm devices, are suitable imaging methods in the framework of the invention.

As the aforementioned measure, a therapy measure can be presented dependent on the comparison, such a pharmaceutical measure or an operative measure.

Alternatively, the measure can mean a new examination of the blood vessel of interest. Preferably a point in time or time interval is proposed for the new examination dependent on the comparison. Preferably, the larger the first indicator value is, the sooner the point in time generated, or the smaller the time interval generated (i.e., the two are inversely proportional).

A preferred embodiment is based on the recognition that the indicator number is also suitable for long-term observation in particular for preventative examinations of healthy patients or for follow-up monitoring of patients in therapy. The preferred embodiment thus concerns a method that in particular is suitable for early recognition and/or progression monitoring in the therapy of a pathological change of the blood vessel of interest of the patient, for example, in the context of coronary heart disease. In the preferred embodiment of the method, 1. the aforementioned first indicator value is stored in a storage medium, preferably together with a location marking for retrieval of the blood vessel of interest,
2. at a second point in time a minimum number of days after the first point in time, a pixel-based or voxel-based second image is acquired of the blood vessel of interest of the patient by means of an imaging method, preferably with the stored location marking from the exposure of the first image being used for image positioning,
3. a measurement for a quantity of existing non-calcified plaque and a measurement for a quantity of existing calcium-rich plaque are determined from the second image, and
4. a second indicator value is determined from the quantities of the different plaque types that represents a measurement of the quantity and the composition of the plaque present in the blood vessel at the second point in time.

The invention also recognizes that the initially specified method is also of particular advantage without the steps d) and e), i.e., with steps 1 through 4 above following instead after step c).

The storage medium can belong to a stationary computer or patient file system, or with particular advantage (with regard to a patient) to an individual, transportable storage card, for example a chip card or magnetic card.

The second indicator value preferably is displayed on an output unit associated with an electronic data processing device in a manner so that its change with regard to the first indicator value is visible as an indication of the change of the plaque in the blood vessel, in particular a difference of the indicator values is displayed on the output unit.

A difference of the indicator values also can be used in order to suggest on an output unit, by means of an electronic data processing device, a change with regard to a measure to by undertaken on the patient.

With particular advantage, a measurement of the quantity of existing fibrous plaque and a measurement of the quantity of existing vascular lumen are determined from the first image in addition to the measurement of the quantity of existing non-calcified plaque and the measurement of the quantity of existing calcium-rich plaque, with the first indicator value being determined from the quantities of the different plaque types.

In the method according to the invention, the imaging method can be based on the principle of computed tomography, the principle of magnetic resonance, the principle of angiography and/or the principle of measurement with ultrasound. It is also possible to combined these methods among one another un order to develop an image of the blood vessel of interest in which both lipids and calcified plaques can be differentiated and quantified with good precision.

In a preferred embodiment, multi-slice computed tomography is used as the imaging method, preferably with prior addition of a contrast agent for contrast enhancement of the vascular lumen. The invention is based on the recognition that calcified plaques are identifiable without contrast means, and that the detection of high-degree stenosis (narrowing), as well as a differentiated depiction of calcified and non-calcified plaques, are also possible in the same image by means of high-resolution contrast-enhancing CT angiography of the coronary arteries.

In particular, ECG-gated multi-slice computed tomography can be used for the examination of vessels of the heart, specifically the coronary arteries.

A particularly good automated differentiation of the different plaque types is thereby possible. To determine the respective quantities, a classification (segmentation) of image parts, in particular of parts of the blood vessel of interest, can be undertaken using the CT number, whereby the classification ensues at least into the four following classes:

I.) non-calcified or lipid plaque: if the CT number lies within a first interval.
II.) fibrous plaque: if the CT number lies within a first interval.
III.) vascular lumen, in particular coronary lumen: if the CT number lies within a third interval,
IV.) calcified plaque: if the CT number lies within a fourth interval.

With this categorization, it is therefore possible—in a semi-automatic or automatic segmentation algorithm—to identify and to typify the contrast-enhancing vascular lumen as well as the plaque contained in the vessel wall.

According to a proposal by G. N. Hounsfield, it has become typical to transform the values of the linear degradation coefficients $\mu$ (measured in $cm^{-1}$) on a dimensionless scale in which water has a value of 0 and air has a value of $-1000$. The conversion formula on the "CT number" (CT density value) is:

$$CTnumber = \frac{\mu - \mu_{water}}{\mu_{water}} 1000 \tag{1}$$

The unit of the CT number is called a "Hounsfield Unit" (HU). This scale, designated as a "Hounsfield scale" is very well suited for the representation printing form anatomical tissue, since the unit HU expresses the deviation in per mil (per thousand) of $\mu_{water}$ and the $\mu$ values of most bodily substances differ only slightly from the $\mu$ value of water. For the most part, only whole numbers from the number range (from $-1000$ for air up to approximately 3000) are used as carriers of the image information.

With particular advantage, the intervals drawn on for segmenting do not overlap and in particular cover a range of the CT number from $-50$ to $1000$ without interruption. With this, an automation of can be particularly simply achieved.

A particularly high diagnostic content is achieved for the indicator value or the indicator values in an embodiment wherein for their determination, a ratio of a first quantity of existing plaque of a first type and a second quantity of existing plaque of a second type different from the first type is used.

The measurement ranges for the quantities of existing plaque of different types that are used in the determination of the indicator value or the indicator values are, with particular advantage for the significance of the indicator value, masses of the existing plaques. Volumes of the existing plaques can also be used. Masses together with volumes preferably are used.

The above object with regard to the device is achieved according to the invention by a data processing device which is preferably connected or associated with an imaging medical examination device (hardwired or wireless) for the purpose of data transmission, and that is operable for implementation of the method according to the invention.

DESCRIPTION OF THE PREFERRED EMBODIMENTS

Figure 1:
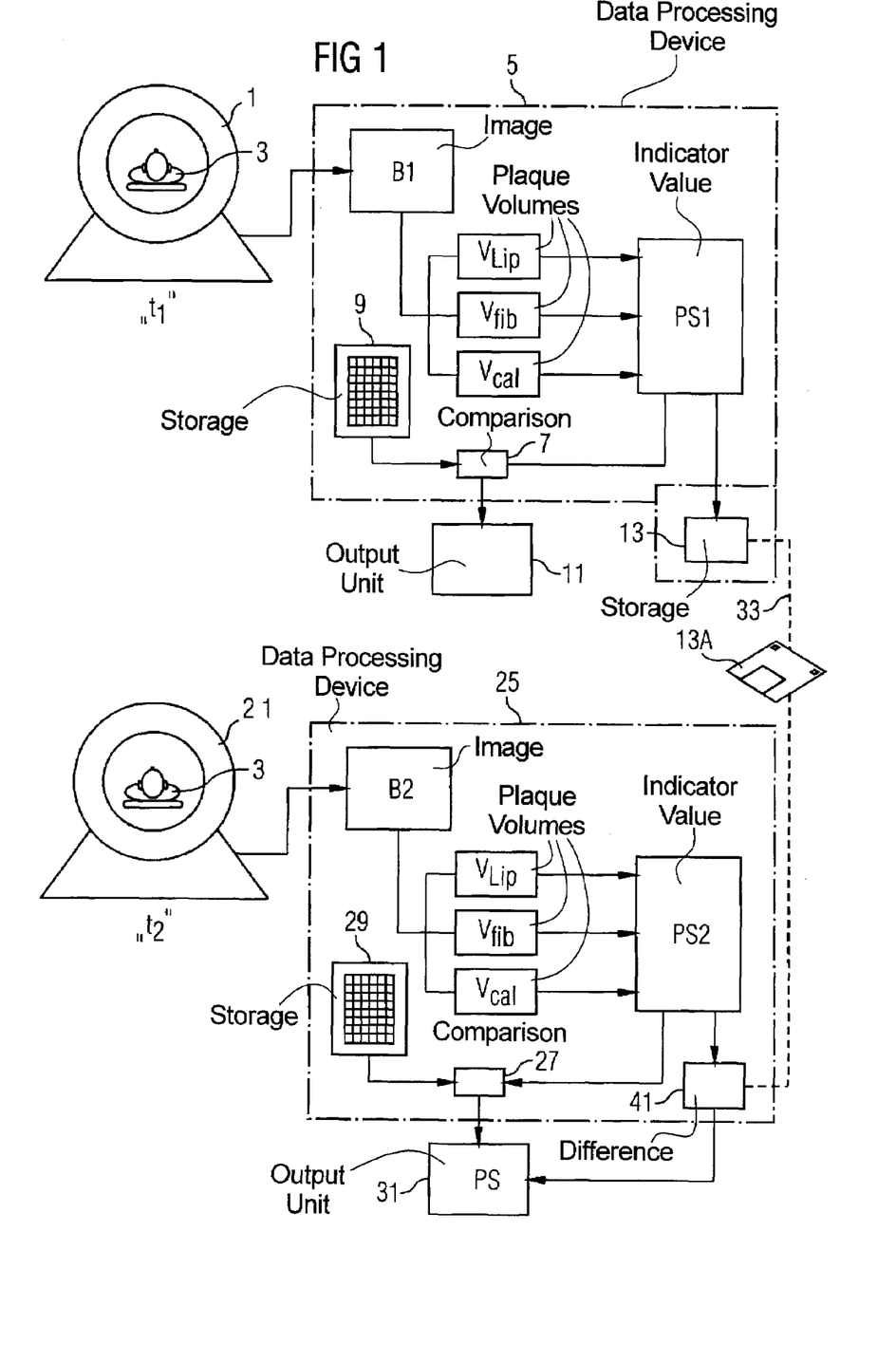
FIG. 1 schematically illustrates a first exemplary embodiment for the method according to the invention partly as a block diagram.

As shown in FIG. 1, at a first point in time $t_1$ a patient 3 is put in a first imaging medical examination device 1 (here a multi-slice spiral CT device with ECG-gated image processing), in the framework of a preventative medical examination such as a heart examination. A digital first CT image B1 is reconstructed from raw data generated by a measurement system of the CT device, by a first data processing device 5 associated with the examination device 1. The examination ensues with regards to a potential pathological or risky change of the coronary blood vessels of the patient 3, in particular with regard to heart disease. A contrast means was administered to the patient 3 before the beginning of the examination.

To support the diagnosis, the contrast-enhanced coronary lumen as well as the plaque comprised in the vessel wall are identified in the first image B1 by means of a semi-automatic or automatic segmentation algorithm. Use is made of the fact that plaques differ in their CT number dependent on their material composition. Lipid-rich plaques (i=lip) have lower density values in the range of the values of water, calcified plaques (i=cal) have in contrast higher density values in the range of the density values of bones. The plaques can therefore be differentiated according to plaque types i. Contrast-enhanced lumen, lipid-rich plaques, fibrous plaques (i=fib) and calcified plaques are differentiated (segmented) using the following threshold operation and marked differently, for example colored, in the visual depiction of the image B1:

I.) non-calcified plaque: −50 HU≦CT number<+50 HU

II.) fibrous plaque: +50 HU≦CT number<+150 HU

III.) vascular lumen: +150 HU≦CT number<+300 HU

IV.) calcified plaque: +300 HU≦CT number<+1000 HU

Finally, the plaque types i, meaning the segments I.), II.) and IV.) are quantified. As a measurement of the quantities of the existing different plaque types i, volumes $V_{cal}$, $V_{fib}$, $V_{lip}$ and masses $M_{cal}$, $M_{fib}$, $M_{lip}$ are calculated:

$$V_i = \sum_n V_i(n) = \sum_n Area_i(n) \cdot Inc \quad \text{for } i = fib, cal, lip \quad (2)$$

$$M_i = \sum_n M_i(n) = \sum_n Area_i(n) \cdot Inc \cdot \rho_i\overline{(CTnumber(n))} \quad (3)$$

for $i = fib, cal, lip$

The calculation ensues for each type i by adding individual lesions n (number index). $Area_i(n)$ thereby means the surface of a lesion n of the type i, Inc present in a slice, the CT slice increment and $\rho_i\overline{(CTnumber(n))}$ means the average density of the lesion n of the type i, whereby the average density depends on the measured CT number.

A first indicator value PS1 is generated from the thusly determined volumes $V_{cal}$, $V_{fib}$, $V_{lip}$ and masses $M_{cal}$, $M_{fib}$, $M_{lip}$ of the different plaque types i that represents a comprehensive measurement of the quantity and the composition of the plaque present in the examined blood vessel at the first point in time $t_1$, and thus can be used on as a statement about the coronary status. Generally, the first indicator value PS1 is calculated as a function of the determined volumes $V_{cal}$, $V_{fib}$, $V_{lip}$ and masses $M_{cal}$, $M_{fib}$, $M_{lip}$ by the data processing device 5.

$$PS1 = f(V_{cal}, V_{fib}, V_{lip}, M_{cal}, M_{fib}, M_{lip}) \quad (4)$$

The indicator value PS1 is particularly well suited as a measurement of the absence or presence of a KHK or of the risk of a coronary event, in the case that it is calculated from the relationships of the plaque volumes $V_{cal}$, $V_{fib}$, $V_{lip}$ and/or the plaque masses $M_{cal}$, $M_{fib}$, $M_{lip}$ of the different types i:

$$PS1 = F_1 \cdot \frac{V_{lip} + V_{0,lip}}{V_{fib} + V_{0,fib}} + F_2 \cdot \frac{V_{lip} + V_{0,lip}}{V_{cal} + V_{0,cal}} + F_3 \cdot \frac{V_{fib} + V_{0,fib}}{V_{cal} + V_{0,cal}} \quad (5)$$

$F_1$, $F_2$ and $F_3$ in the data processing device represent adjustable weighting factors that are, however, established unchangeable weighting factors for comparing examinations. A corresponding calculation rule is valid for the masses, such that the formula for PS1 can include either three analogous terms for the masses, or alternatively six summation terms altogether. The indicator value PS1 is a measurement independent of general risk factors (for example, blood-lipid value, high blood pressure, family medical history, etc.) that described the current vessel status and the risk of a coronary event connected therewith.

In a comparison step 7, the first indicator value PS1 is compared with limit values $PS_O$, $PS_I$, $PS_{II}$, $PS_M$, and a proposal for the further procedure is output on a first output unit 11 (for example monitor, printer) associated with the electronic data processing device 5. Various end points of the CT examination are proposed:

exclusion (preclusion) of a disease indication for an interventional therapy given an advanced disease pharmacological treatment for preventative therapy in the pre-clinical stage (therapy in various marked stages).

Figure 2:
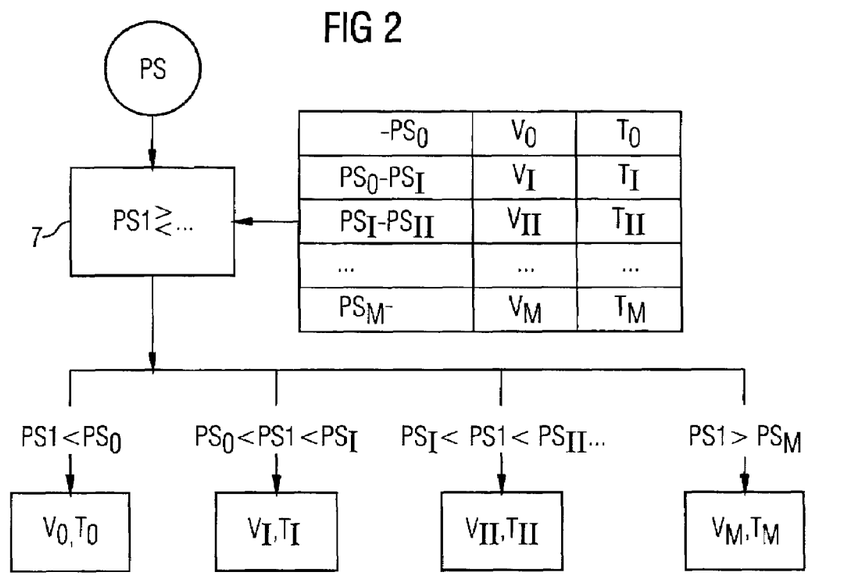
FIG. 2 in detail a step of the method according to FIG. 1

The procedure in the comparison operation 7 is shown in detail in FIG. 2. In the table in the first register 9, intervals are established via lower limit values and upper limit values for the indicator value PS1, and for each interval a proposal appears for a therapy measure $V_O$, $V_I$, $V_{II}$, $V_M$ as well as a proposal for a time interval $T_O$, $T_I$, $T_{II}$, $T_M$, after the duration of which a new examination is advised:

| Lower limit value for PS1 | Upper limit value for PS1 | Therapy proposal | Time interval |
|---|---|---|---|
|  | $PS_O$ | $V_O$ | $T_O$ |
| $PS_O$ | $PS_I$ | $V_I$ | $T_I$ |
| $PS_1$ | $PS_{II}$ | $V_{II}$ | $T_{II}$ |
| ... | ... | ... | ... |
| $PS_M$ |  | $V_M$ | $T_M$ |

The indicator value PS1 determined according to equation (4) or (5) is compared with the interval boundaries, and the proposal of a therapy measure $V_O$, $V_I$, $V_{II}$, $V_M$ belonging to the related interval and the appertaining proposal for a time interval $T_O$, $T_I$, $T_{II}$, $T_M$ are presented on the output unit 11.

Denoted, for example, are:

$V_O$: exclusion of a disease, no therapy; however, new examination (follow-up) in $T_O$=12 months;

$V_I$: indication for preventative light medication therapy; new examination (follow-up) in $T_I$=9 months;

$V_{II}$: indication for preventative strong medication therapy; new examination (follow-up) in $T_{II}$=6 months;

$V_M$: indication for interventional therapy; new examination (follow-up) in $T_M$=2 months.

As can be seen from FIG. 1, the first indicator value PS1 is stored on a storage medium 13, for example in an electronic patient file.

On the storage medium 13, a location marking to retrieve the blood vessel of interest is also stored with it.

Figure 3:
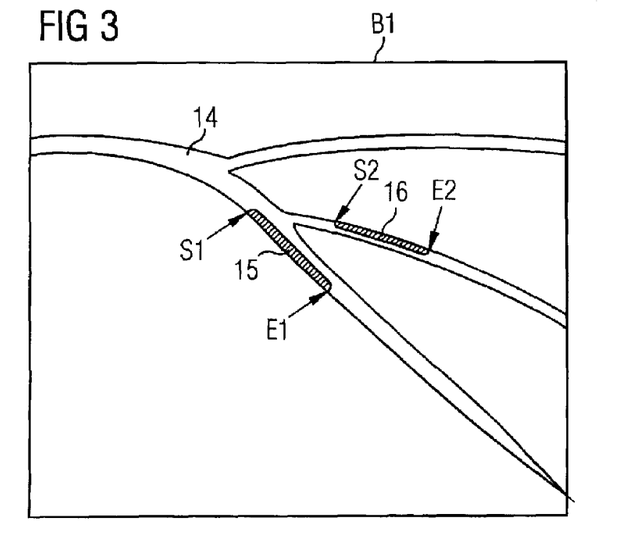
FIG. 3 shows, in the method according to FIG. 1, an evaluated image of a blood vessel tree, and FIG. 4 schematically illustrates a second exemplary embodiment for the method according to the invention partly as a block diagram.

In the examination, identified plaques are marked by anatomical or distance landmarks. As is illustrated in the image B1 in FIG. 3 for a schematically depicted blood vessel tree 14, a start make S1, S2 and an end mark E1, E1 are stored for each plaque 15, 16 along the vessel that define the position and maximum dimension of the lesion in the vessel tree. In a later examination in the framework of a follow-up or a progression examination, the region of interest (=ROI) and the plaque can thus be reproducibly repositioned or located, and thus quantitatively evaluated anew.

The storage medium 13 can belong to a data processing device, connected with it via a network, or can be fashioned as a transportable storage medium 13A (diskette, chip card, etc.)

In a follow-up examination (ensuing a number of weeks, in particular at least one or more months later (second point in time "$t_2$" in FIG. 1)), a second image B2 is acquired of the blood vessel of interest of the patient 3 by means of a second imaging medical examination device 21 (here likewise a CT device) that can be, but is not required to be, identical to or of the same type as the first imaging medical examination device 1. A repositioning algorithm positions the measurement system of the CT device semi-automatically or automatically using the location marking stored in the storage medium 13.

In a second data processing device 25 associated with the second imaging medical examination device 21, in an analog manner to evaluate the first image B1, a second indicator value PS2 is calculated from the second image B2, compared in a comparison step 27 with the limit values $PS_O$, $PS_I$, $PS_{II}$, $PS_M$ likewise stored in a second storage medium 29, and a proposal for a therapy measure $V_O$, $V_I$, $V_{II}$, $V_M$ as well as a proposal for a time interval $T_O$, $T_I$, $T_{II}$, $T_M$ are displayed on a second output unit 31.

The second data processing device 25 is connected with the first data processing device 5 either via a data line 33 or with the storage medium 13, or it has a reading device (not shown) to read the information stored on the transportable storage medium 13A.

Additionally, a difference $\Delta PS = PS2 - PS_1$ of the indicator values $PS_1$, $PS_2$ is calculated by the second data processing device 25 in a difference step 41 and shown on the output unit 31. A change with regard to the first indicator value PS1 is thereby visible as an indication for the change of the plaque in the blood vessel. For example, after a therapy with lipid suppressors that aim at stabilizing potentially unstable plaque or at the regression of advanced lesions, a successful treatment would be reflected in a reduced indicator value PS2 with regard to the first indicator value PS1.

Figure 4:
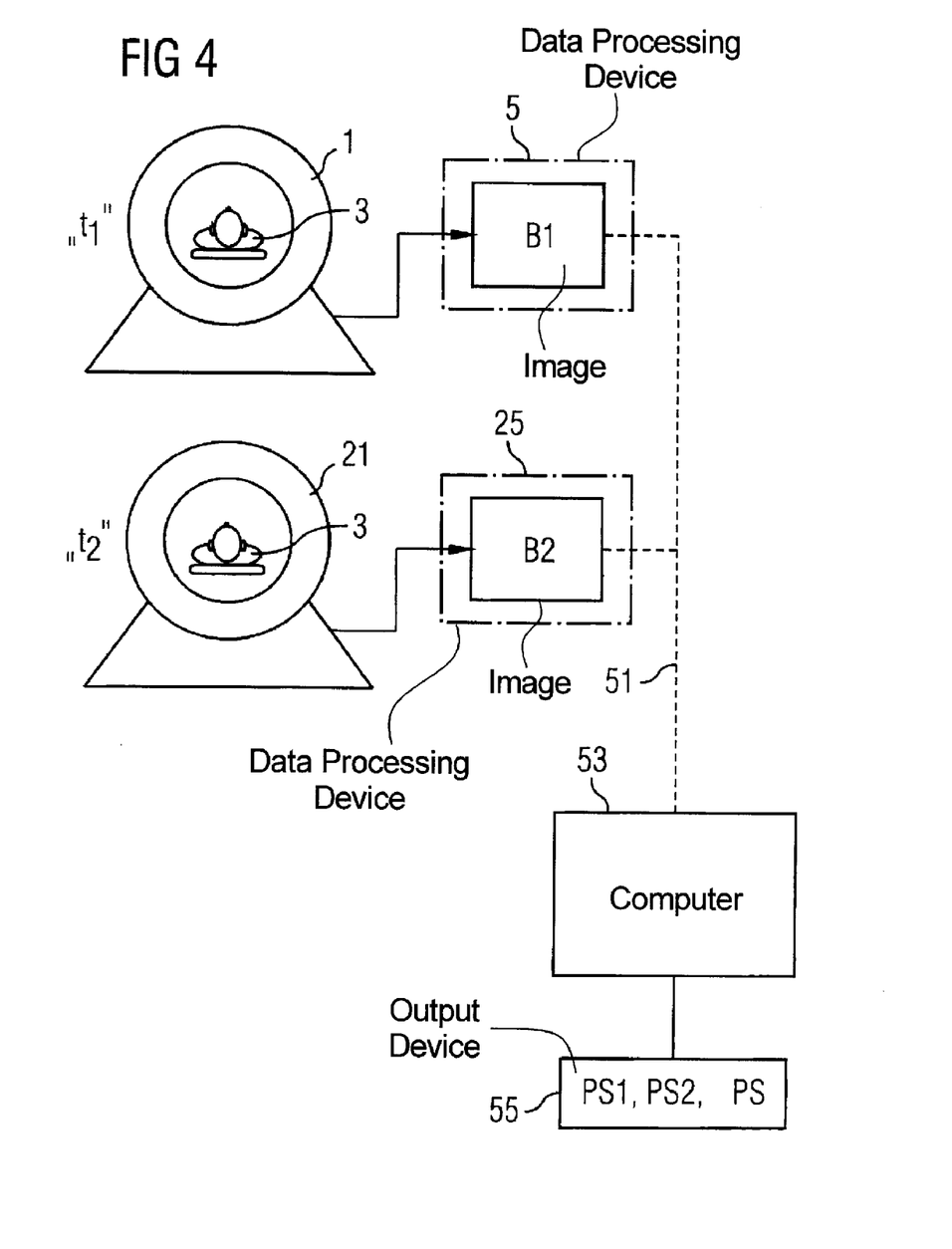

The second exemplary embodiment shown in FIG. 4 for the method according to the invention is identical with that of FIG. 1 to a large extend, with the difference that only the image reconstruction ensues in the data processing device 5, 25 of the CT device 1 or 21 used for the repeated CT examination. After the image reconstruction, the images B1, B2 are transmitted via a data network 51 to a central computer 53 in which the same calculation methods respectively for each image B1, B2 (in particular using the same intervals for the CT values), the same limit values $PS_O$, $PS_I$, $PS_{II}$, $PS_M$ and the same calculation formula for the indicator value, the respective indicator value PS1 or, respectively, PS2 as well as their difference $\Delta PS$ are calculated and presented on an appertaining output unit 55. The central computer 53 can be a self-contained system or a part of a system with which the electronic patient files are administrated.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for supporting at least one of diagnosis and therapy of a pathological change of a blood vessel in a subject, comprising the steps of:
   (a) at a point in time, acquiring a single image of a blood vessel using an imaging modality, said single image being selected from the group consisting of pixel images and voxel images;
   (b) from said single image, making a measurement of an existing quantity of non-calcified plaque and a measurement of an existing quantity of calcium-rich plaque associated with the blood vessel;
   (c) determining an indicator value dependent on the respective quantities of non-calcified plaque and calcium-rich plaque from said measurement, and on the composition of said plaque in said blood vessel at said point and time;
   (d) storing at least one limit value in a data processor and, in said data processor, comparing said indicator value with said at least one limit value to obtain a comparison result; and
   (e) at an output unit associated with said data processor, presenting an output proposal dependent on said comparison result, selected from the group consisting of a proposal for a measure to be undertaken on the patient and a proposal for no measure.

2. A method as claimed in claim 1 wherein step (e) comprises presenting a therapy measure at said output unit as said proposal for a measure to be undertaken on the patient.

3. A method as claimed in claim 2 comprising presenting, as said therapy measure, a therapy measure selected from the group consisting of a pharmaceutical measure and an operative measure, dependent on said comparison result.

4. A method as claimed in claim 1 wherein step (e) comprises presenting a proposal at said output unit for a new examination of the blood vessel as said proposal for a measure to be undertaken on the patient.

5. A method as claimed in claim 4 comprising including, in said proposal for a new examination of the blood vessel, a time frame for implementing said new examination, selected from the group consisting of a point in time and a time interval, dependent on said comparison result.

6. A method as claimed in claim 5 comprising selecting said time frame to be inversely proportional to said indicator value.

7. A method as claimed in claim 1 wherein said point in time is a first point in time, said single image is a first single image, and said indicator value is a first indicator value, and comprising the additional steps of:
  storing said first indicator value in a storage medium accessible by said data processor, together with a location marking designating a position of the blood vessel in said first single image;
  at a second point in time following said first point in time by a minimum of two days, acquiring a second single image of the blood vessel with an imaging modality, using said location marking to correlate a position of the blood vessel in the single second image with a position of the blood vessel in the single first image, said single second image being selected from the group consisting of poxel images and voxel images;
  making a measurement of a quantity of said non-calcified plaque and a quantity of said calcium-rich plaque from said second single image; and
  determining a second indicator value from the respective quantities of said non-calcified plaque and said calcium-rich plaque in said measurement from said second single image, representing a measurement of a quantity and a composition of plaque in the blood vessel at said second point in time.

8. A method as claimed in claim 7 comprising including said second indicator value in the presentation at said output unit with an indication, relative to said first indicator value, of a change of said plaque in the blood vessel between said first point in time and said second point in time.

9. A method as claimed in claim 8 comprising displaying at said output unit a difference between said first indicator value and said second indicator value as said indication of said change.

10. A method as claimed in claim 7 comprising measuring the respective quantities of non-calcified plaque and calcium-rich plaque for determining said first indicator by measuring a mass and a volume of said non-calcified plaque from said first single image and measuring a mass and a volume of said calcium-rich plaque from said first single image, and measuring the respective quantities of non-calcified plaque and calcium-rich plaque for determining said second indicator by measuring a mass and a volume of said non-calcified plaque in said second single image and measuring a mass and a volume of said calcium-rich plaque in said second single image.

11. A method as claimed in claim 1 comprising employing, as said imaging modality in step (a), an imaging modality selected from the group consisting of computed tomography, magnetic resonance imaging, and geography and ultrasound.

12. A method as claimed in claim 1 comprising employing, as said imaging modality in step (a), multi-slice computed tomography.

13. A method as claimed in claim 12 comprising the additional step of administering a contrast agent for contrast enhancement of vascular vessels in said multi-slice computed tomography modality.

14. A method as claimed in claim 1 wherein step (c) comprises from said image, making a further measurement of a quantity of fibrous plaque in the blood vessel and a quantity of open lumen in the blood vessel, and determining said indicator value from said quantity of fibrous plaque and quantity of open lumen in addition to said quantity of non-calcified plaque and said quantity of calcium-rich plaque.

15. A method as claimed in claim 14 comprising determining a CT number for the blood vessel in the image and determining the respective quantities of non-calcified plaque, calcium-rich plaque, fibrous plaque and open vascular lumen, dependent on said CT number by classification as non-calcified plaque if said CT number is within a first interval, as fibrous plaque if said CT number is within a second interval, as a vascular open lumen if said CT number is within a third interval, and as calcified plaque if said CT number is within a fourth interval.

16. A method as claimed in claim 15 wherein said first, second, third and fourth intervals do not overlap and cover, without gaps, a range of said CT number between −50 and 1000.

17. A method as claimed in claim 1 wherein step (c) comprises determining said indicator value as a ratio of the respective quantities of said non-calcified plaque and said calcium-rich plaque in said single image.

18. A method as claimed in claim 1 wherein step (c) comprises measuring said quantity of said non-calcified plaque by determining a mass and a volume of said non-calcified plaque from said image, and measuring said quantity of calcium-rich plaque by determining a mass and a volume of said calcium-rich plaque from said single image.

19. A data processing device for supporting at least one of diagnosis and therapy of a pathological change of a blood vessel in a subject, said data processor being supplied with a single image of a blood vessel acquired at a point in time using an imaging modality, said single image being selected from the group consisting of pixel images and voxel images, and said data processor being programmed to:
  from said single image, make a measurement of an existing quantity of non-calcified plaque and a measurement of an existing quantity of calcium-rich plaque associated with the blood vessel;
  determine an indicator value dependent on the respective quantities of non-calcified plaque and calcium-rich plaque from said measurement, and on the composition of said plaque in said blood vessel at said first point in time;
  compare said indicator value with said at least one stored limit value to obtain a comparison result; and
  at an output unit associated with said data processor, present an output proposal dependent on said comparison result, selected from the group consisting of a proposal for a measure to be undertaken on the patient and a proposal for no measure.

20. A data processing device as claimed in claim 19 programmed to present a therapy measure at said output unit as said proposal for a measure to be undertaken on the patient.

21. A data processing device as claimed in claim 20 programmed to present as said therapy measure, a therapy measure selected from the group consisting of a pharmaceutical measure and an operative measure, dependent on said comparison result.

22. A data processing device as claimed in claim 19 programmed to present a proposal at said output unit for a new examination of the blood vessel as said proposal for a measure to be undertaken on the patient.

23. A data processing device as claimed in claim 22 programmed to include, in said proposal for a new examination of the blood vessel, a time frame for implementing said new examination, selected from the group consisting of a point in time and a time interval, dependent on said comparison.

24. A data processing device as claimed in claim 23 programmed to select said time frame to be inversely proportional to said indicator value.

25. A data processing device as claimed in claim 19 wherein said point in time is a first point in time, said image is a first single image, and said indicator value is a first indicator value, and wherein said data processing device is supplied with a second single image acquired at a second point in time following said first point in time by a minimum of two days, of the blood vessel with an imaging modality, using said location marking to correlate a position of the blood vessel in the second single image with a position of the blood vessel in the first single image, said second single image being selected from the group consisting of poxel images and voxel images and wherein said data processing device is programmed to:
   store said first indicator value in a storage medium accessible by said data processor, together with a location marking designating a position of the blood vessel in said first single image;
   make a measurement of a quantity of said non-calcified plaque and a quantity of said calcium-rich plaque from said second single image; and
   determine a second indicator value from the respective quantities of said non-calcified plaque and said calcium-rich plaque in said measurement from said second single image, representing a measurement of a quantity and a composition of plaque in the blood vessel at said second point in time.

26. A data processing device as claimed in claim 25 programmed to include said second indicator value in the presentation at said output unit with an indication, relative to said first indicator value, of a change of said plaque in the blood vessel between said first point in time and said second point in time.

27. A data processing device as claimed in claim 26 programmed to display at said output unit a difference between said first indicator value and said second indicator value as said indication of said change.

28. A data processing device as claimed in claim 19 programmed to measure the respective quantities of non-calcified plaque and calcium-rich plaque for determining said first indicator by measuring a mass and a volume of said non-calcified plaque from said first single image and measuring a mass and a volume of said calcium-rich plaque from said first image, and to measuring the respective quantities of non-calcified plaque and calcium-rich plaque for determining said second indicator by measuring a mass and a volume of said non-calcified plaque in said second single image and measuring a mass and a volume of said calcium-rich plaque in said single second image.

29. A data processing device as claimed in claim 19 programmed to make a further measurement from said image of a quantity of fibrous plaque in the blood vessel and a quantity of open lumen in the blood vessel, and determine said indicator value from said quantity of fibrous plaque and quantity of open lumen in addition to said quantity of non-calcified plaque and said quantity of calcium-rich plaque.

30. A data processing device as claimed in claim 29 programmed to determine a CT number for the blood vessel in the image and determining the respective quantities of non-calcified plaque, calcium-rich plaque, fibrous plaque and open vascular lumen, dependent on said CT number by classification as non-calcified plaque if said CT number is within a first interval, as fibrous plaque if said CT number is within a second interval, as a vascular open lumen if said CT number is within a third interval, and as calcified plaque if said CT number is within a fourth interval.

31. A data processing device as claimed in claim 30 programmed to employ first, second, third and fourth intervals that do not overlap and cover, without gaps, a range of said CT number between −50 and 1000.

32. A data processing device as claimed in claim 19 programmed to determine said indicator value as a ratio of the respective quantities of said non-calcified plaque and said calcium-rich plaque.

33. A data processing device as claimed 19 programmed to measure said quantity of said non-calcified plaque by determining a mass and a volume of said non-calcified plaque from said image, and measure said quantity of calcium-rich plaque by determining a mass and a volume of said calcium-rich plaque from said single image.

\* \* \* \* \*